United States Patent [19]

Dimpfl

[11] Patent Number: 4,486,535
[45] Date of Patent: Dec. 4, 1984

[54] METHOD AND APPARATUS FOR MEASURING PARTICLE SIZE

[75] Inventor: William L. Dimpfl, Oakland, Calif.

[73] Assignee: Chevron Research Company, San Francisco, Calif.

[21] Appl. No.: 366,236

[22] Filed: Apr. 7, 1982

[51] Int. Cl.[3] ............................................ G01N 15/02
[52] U.S. Cl. ...................................... 436/2; 436/145; 436/155; 356/335
[58] Field of Search .................... 356/335; 436/2, 155, 436/160, 145

[56] References Cited

U.S. PATENT DOCUMENTS

| | | | |
|---|---|---|---|
| 3,518,001 | 6/1970 | Hell | 356/87 |
| 3,680,961 | 8/1972 | Rudd | 356/102 |
| 3,740,149 | 6/1973 | Whetten | 356/102 |
| 3,790,282 | 2/1974 | Fielding | 356/86 |
| 3,825,345 | 7/1974 | Lorenz | 356/85 |
| 3,851,169 | 11/1974 | Faxvog | 250/222 PC |
| 3,860,345 | 1/1975 | Railléere et al. | 356/87 |
| 4,021,117 | 5/1977 | Göhde et al. | 356/39 |
| 4,279,512 | 7/1981 | Tunstall | 356/335 |

FOREIGN PATENT DOCUMENTS 2064763  6/1981  United Kingdom ................ 436/155

Primary Examiner—Hiram H. Bernstein
Attorney, Agent, or Firm—Burns, Doane, Swecker & Mathis

[57] ABSTRACT

The disclosure relates to an apparatus for measuring the size of gas entrained particles by detecting the rate of incandescent burning of the particles. Entrained particles are passed at a controlled velocity through a heated zone where they are gradually consumed. The radiant energy emitted by the burning particles is detected at varying locations along the path of flow through the heated zone. An indication of particle size distribution is obtained by deriving the third derivative of detected radiant energy intensity with respect to distance of flow through the heated zone.

2 Claims, 4 Drawing Figures ond distance signal functionally related to the distance between the detection zone and the inlet. A circuit responsive to the first and second signals produces an output signal functionally related to the third derivative of detected radiant energy intensity with respect to the distance between the detection zone and the inlet as an indication of the size distribution of the particles.

The gas-suspended particles may be introduced into the apparatus by sampling gas-suspended carbonaceous particles from the stream such as a stream of combustion product. A conduit is provided for maintaining the sampled, gas-suspended particles at a temperature below the burning temperature of the carbonaceous particles prior to introduction into the burning chamber through the inlet. Oxygen may be added to the sampled, gas-suspended particles prior to introduction into the burning chamber.

In a preferred embodiment, the photodetector may include a cooled mirror extending around the periphery of the detection zone; a photomultiplier tube optically exposed to the mirror and detection zone; and baffles for optically shielding the photomultiplier tube from exposure to surfaces of the burning chamber.

In a preferred embodiment of the present invention, the indication of the size distribution of the particles is produced by a circuit including differentiating circuits and dividing circuits which process the photodetector signal and the distance signal in order to produce an output signal functionally related to the third derivative of the detected light intensity with respect to the distance between the detection zone and the inlet. An X-Y recorder may be provided in which the distance signal controls deflection along one axis and the output signal from the processing circuit controls deflection along the other axis, whereby a graphical recording is made as an indication of the size distribution of the particles. Further aspects and details of the present invention will be apparent from the detailed description given below.

DETAILED DESCRIPTION

Figure 1:
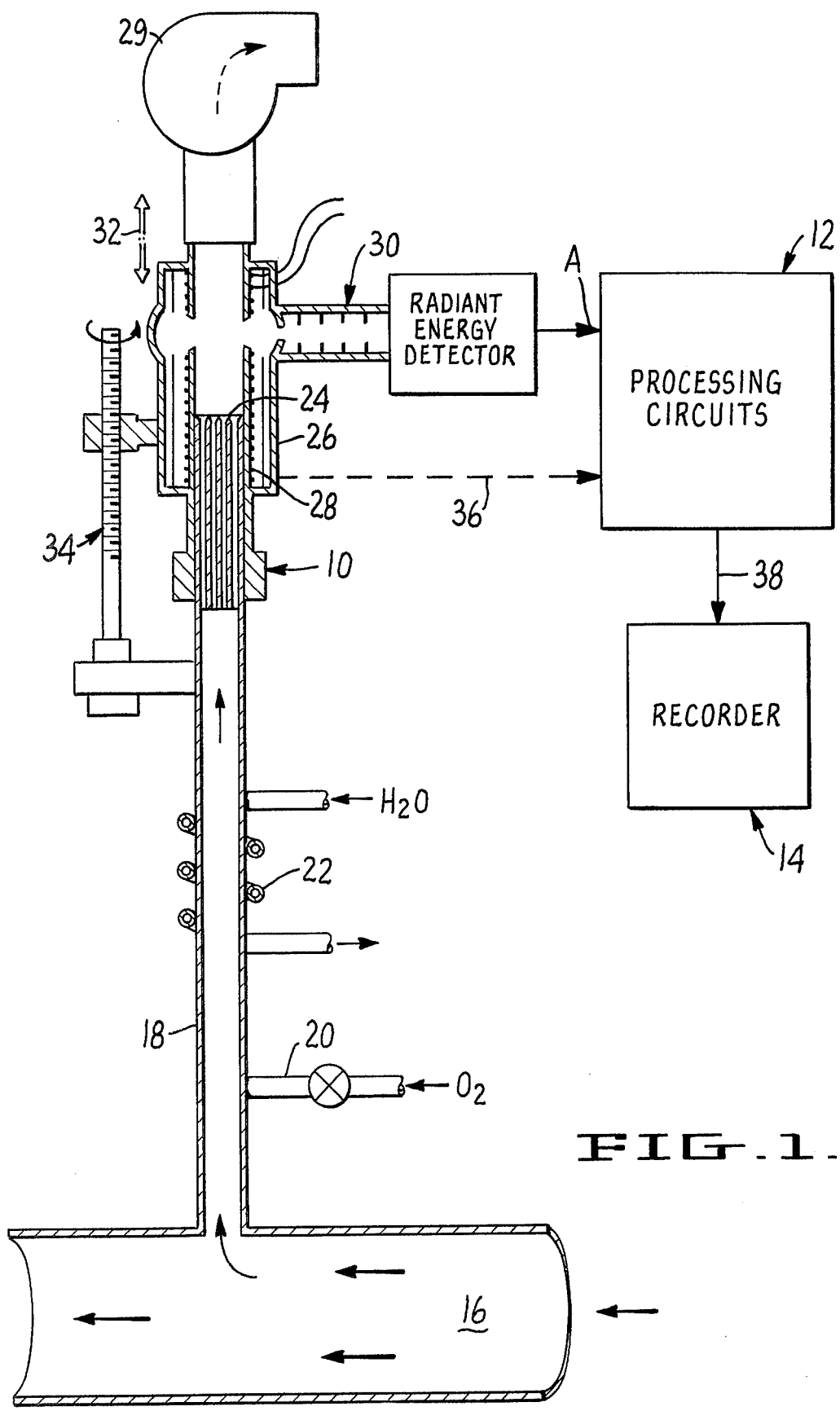
FIG. 1 is a schematic diagram in partial cross-section of an apparatus for measurement of the continuous size distribution of gas-suspended particles, according to a preferred embodiment of the present invention.

The present invention employs the technique of measuring light emitted by burning particles, in such a way that size distribution of the particles can be determined therefrom. The burning particles decrease in size as they burn with a consequent reduction in light output. It is this reduction of intensity with time which provides the functional basis for producing indications of particle size distribution.

The following mathematical derivation will help to clarify the operation of the present invention.

For purposes of this derivation the following assumptions are made:

1. The gas-suspended particles whose size distribution are to be measured are spherical.
2. The rate at which a particle's volume decreases by burning is proportional to its surface area.
3. Particle burning does not significantly affect its temperature or radiant emission.

The first assumption is good for fresh combustion exhaust. The second assumption should be good for particles which are large in proportion to the boundary layer of exchanging gases around them. Finally, the third assumption can be made good by carefully controlling the conditions of the measurement.

The derivation is developed by establishing the radiant intensity as a function of time of a particle which is decreasing in size by burning. This functionality is used to establish the relationship describing the radiant intensity as a function of time from a given distribution of different sized particles. As will be discussed, this relationship may be used to extract particle size distribution information from light intensity measurements.

The time rate of change of light from a burning particle is proportional to the time rate of change of its surface area:

$$\frac{dl}{dt} = \alpha \frac{d}{dt} 4\pi r^2 = 8\alpha \pi r \frac{dr}{dt} \quad (1)$$

where $l$ is light intensity, $\alpha$ is the proportionality constant, and $r$ is the radius of the spherical particle.

If a spherical particle's volume decreases at a rate proportional to its surface area, (a reasonable approximation for burning) then:

$$\frac{dV}{dt} = -4\beta\pi r^2 \quad (2)$$

where $V$ is the particle volume and $\beta$ is the proportionality constant. But from the volume formula for a sphere:

$$\frac{dV}{dt} = 4\pi r^2 \frac{dr}{dt} \quad (3)$$

so $$\frac{dr}{dt} = -\beta \quad (4)$$

Integrating and imposing $r = r_o$ at $t = 0$ yields $$r = r_o - \beta t \quad (5)$$

Substituting Equations (4) and (5) into Equation (1) yields:

$$dl = -8\alpha\beta\pi(r_o - \beta t)dt \quad (6)$$

Integrating this expression and scaling $\alpha$ such that $l = 4\alpha\pi r_o^2$ at $t = 0$ yields:

$$l = 4\alpha\pi r_o^2 \left(\frac{\beta}{r_o} t - 1\right)^2 \quad (7)$$

If $P(r_o)$ is the probability function describing the distribution of particle radii, then the cumulative light intensity $I(t)$ at time $t$ from the particles remaining from the original distribution is:

4,486,535

METHOD AND APPARATUS FOR MEASURING PARTICLE SIZE

BACKGROUND OF THE DISCLOSURE

The present invention relates to method and apparatus for measuring the size of gas-suspended particles. Preferred embodiments of the invention relate to the measurement of the size distribution of carbonaceous particles such as soot or combustion products found in exhaust gases.

Measurement of gas-suspended particles is a subject of growing interest in the field of emission control. A convenient, accurate and inexpensive method for measuring emission particle size distribution is needed in the study of the effects and control of particulate emissions.

In the past, a number of different methods have been taught for the measurement of the size of gas-suspended particles. It has been proposed that particle size be measured by diffusion of light. Such a method is discussed in U.S. Pat. No. 3,825,345 to Lorenz, which notes disadvantages in this technique due to the complex functional relationship between particle size and the signal obtained, and the limitations of the technique due to an unfavorable signal to noise ratio for small particles. Somewhat similar techniques involving the detection of the effect of particles on light directed at them, rather than detecting light emitted by the particles, are taught in U.S. Pat. No. 3,680,961 to Rudd and U.S. Pat. No. 3,851,169 to Faxvog.

A second technique involves measurement of the thermal emission of particles by exposing the particles to a high temperature hydrogen flare. This method is also discussed in U.S. Pat. No. 3,825,345 to Lorenz where it is noted that, using this second technique, particles are singly and consecutively taken to a minute hydrogen flare in which they are evaporated. The particles are said to emit a luminescent flash of an intensity proportional to their mass. Lorenz indicates that this procedure is unsuitable for particle size analysis of atmospheric aerosols and often lacks sensitivity.

Lorenz proposes the use of an atomic absorption spectometer having an evaporating zone small enough to be completely filled by a single evaporated particle. However, in addition to the expense associated with the provision of an atomic absorption spectometer, the method is constrained to detecting particles, one at a time rather than detecting populations of gas suspended particles simultaneously.

U.S. Pat. No. 3,790,282 to Fielding teaches a method of determining the concentration of pollutants in air by exciting atoms of the pollutant by burning the pollutant with a fuel in a pressure chamber and measuring the intensity of the "characteristic light" emitted by the excited atoms. The Fielding patent indicates that from this intensity, the concentration of the pollutant can easily be calculated. The Fielding patent does not teach the measurement of size distribution of the pollutant particles.

It has been proposed to measure gas-suspended particle size distribution by the method of cascading inertial impactors. In such method a series of plates are positioned to intercept a gas stream carrying particles. Each plate is positioned behind an opening of a given size. The openings through successive plates are progressively smaller so that particles inertially adhering to each plate after impact are of different size ranges. After exposure of the plates to a gas-suspended particle stream for a given time, the plates are weighed. The measured weights are plotted against the plate opening size to indicate size distribution of the particles. The method has the disadvantages that it requires long measurement times and does not yield a continuous distribution.

Other art, of more general interest, is found in the following patents: U.S. Pat. No. 3,088,808 to Mandell, Jr.; U.S. Pat. No. 3,518,001 to Hell; U.S. Pat. No. 3,700,330 to Davis; U.S. Pat. No. 3,740,149 to Whetten; U.S. Pat. No. 3,860,345 to Raillere et al; U.S. Pat. No. 4,021,117 to Gohde et al; and U.S. Pat. No. 4,279,512 to Tunstall.

Accordingly, it is a primary object of the present invention to provide a novel, convenient, accurate and inexpensive method and apparatus for measuring gas-suspended particle size distribution.

It is another object of the present invention to provide a novel method and apparatus for measurement of the continuous size distribution of carbonaceous particles suspended in a gas such as an exhaust stream.

It is another object of the present invention to provide a novel method and apparatus to rapidly measure the size distribution of simultaneously detected populations of particles suspended in a gas.

These and other objects and features of the invention will become apparent from the claims, and from the following description when read in conjunction with the accompanying drawings.

SUMMARY OF THE INVENTION

The present invention relates to a method and apparatus for measuring the size distribution of particles entrained in a gas. More particularly, the invention relates to a method and apparatus for measuring the continuous size distribution of gas-suspended carbonaceous particles through induced dynamic burnout incandescence. The measurement is made by first passing the particles and entraining gas through a heated zone to induce incandescent burning of the particles which results in the particles entrained in the gas being gradually consumed as the particles move through the heated zone. The radiant energy emitted by the burning, entrained particles is detected at varying locations along the path of flow of the gas through the heated zone. An indication of the size distribution of the particles entrained in the gas is produced responsive to the rate at which the detected radiant energy varies with the detection location along the path of flow.

In a preferred embodiment of the present invention an apparatus is employed which includes a burning chamber. A conduit is provided for introducing gas-suspended carbonaceous particles through an inlet into the burning chamber, whereupon the gas passes through the burning chamber at a controlled velocity. The burning chamber is heated approximately uniformly along the path of flow of the gas to induce incandescent burning of the particles as the gas passes through the burning chamber. A detector is provided for detecting the radiant energy intensity of the heated particles in a detection zone within the burning chamber. The detector provides a first signal responsive to the detected radiant energy as the distance between the detection zone and the inlet is varied. In a preferred embodiment the distance variation is effected by a screw drive which moves the burning chamber housing relative to a conduit inlet. A sensor is provided which produces a sec- $$I(t) = 4\alpha\pi \int_{\beta t}^{\infty} P(r_o)r_o^2 \left(\frac{\beta}{r_o}t - 1\right)^2 dr_o \quad (8)$$

From the second time derivative of Equation (8):

$$\int_{\beta t}^{\infty} P(r_o)dr_o = \frac{1}{8\alpha\beta^2\pi} \frac{d^2I(t)}{dt^2} \quad (9)$$

$P(r_o)$ can be found by differentiating Equation (9) with respect to $r_o$; and by recognizing that $r_o = \beta t$ at the moment a particle of radius $r_o$ vanishes [from Equation (4)], it follows that:

$$P(r_o) = P(\beta t) = \frac{1}{8\alpha\pi\beta^3} \frac{d^3I(t)}{dt^3} \quad (10)$$

This is the relationship which equates the desired particle size distribution to the measurable radiant intensity as a function of time.

The following describes an apparatus which serves to measure the foregoing intensity distribution.

By passing gas-suspended particles to be analyzed through a tube at a known or controlled velocity v, the intensity of particle radiation as a function of the distance, x, from the entry point is equivalent to the intensity function of Equation (10):

$$P(r_o) = P\left(\frac{\beta x}{v}\right) = \frac{v^3}{8\alpha\pi\beta^3} \frac{d^3I(x)}{dx^3} \quad (11)$$

Thus, the probability function describing the distribution of particle radii can be determined by measuring the intensity $I(x)$ and obtaining its third derivative.

An apparatus suitable for measurement of $I(x)$, according to a preferred embodiment of the present invention, is shown schematically in partial cross-section in FIG. 1. The apparatus includes a gas handling and detector assembly 10 and processing circuits and recorder 12 and 14, respectively.

In a preferred embodiment of the present invention a sample of gas-suspended particles may be withdrawn from a gas stream 16 such as an exhaust stream carrying combustion products or soot. The sampled fraction is drawn into conduit 18 where it is combined with oxygen introduced through oxygen inlet 20. The oxygen flow rate may be selected to optimize the burning rate of all particles. Advantageously, the conduit 18 is made of a good heat conducting material and is cooled by a water cooling coil 22 to maintain the sampled gas fraction at a relatively low temperature at which the gas-suspended particles do not burn. At an end of the conduit 18, one or more openings are provided which serve as an inlet 24 to a burning chamber 26. Advantageously, flow through inlet 24 is non-turbulent to facilitate a uniform treatment of all particles entering the chamber. The construction and arrangement of the burning chamber, inlet port and conduit are discussed in greater detail below in connection with FIG. 2.

The burning chamber 26 is provided with heating coils 28 which are selected and configured to raise the temperature in the burning chamber sufficiently to cause incandescent burning of the gas-suspended particles. Gas is exhausted from the burning chamber by a blower 29. The burning chamber temperature is selected so that the heat generated in burning the particles in the burning chamber does not provide unwanted variations in the particle temperature.

A radiant energy detector assembly 30 is provided for detecting the intensity of radiant energy (typically visible light and/or infrared energy) from heated particles in a detection zone within the burning chamber and for providing a first signal responsive thereto. This first signal is applied to a first terminal A of the processing circuits 12.

As indicated by the double headed arrow 32 of FIG. 1, the inlet 24 of the conduit 18 is movable within the burning chamber 26, while the radiant energy detector 30 is stationary with respect to the burning chamber. The relative motion indicated by the double headed arrow 32 may be imparted by a screw drive mechanism indicated generally by the numeral 34. As the screw of the screw drive is rotated, an upper portion of the conduit 18 slides into or out of the burning chamber 26.

Relative movement of the inlet 24 with respect to the burning chamber is sensed by mechanical or electrical means indicated by the dotted line 36. This sensed movement is converted to an electrical signal employed by the processing circuits 12, as will be discussed in greater detail in connection with FIG. 3 below.

The processing circuits 12 produce an output signal, indicated by arrow 38, which is functionally related to the third derivative of detected light intensity with respect to the distance between the inlet 24 and the region of the burning chamber to which the photodetector assembly is directed. This output signal is an indication of the size distribution of the particles and may be applied to the chart recorder 14 to provide a graphical indication of the size distribution of the particles.

Figure 2:
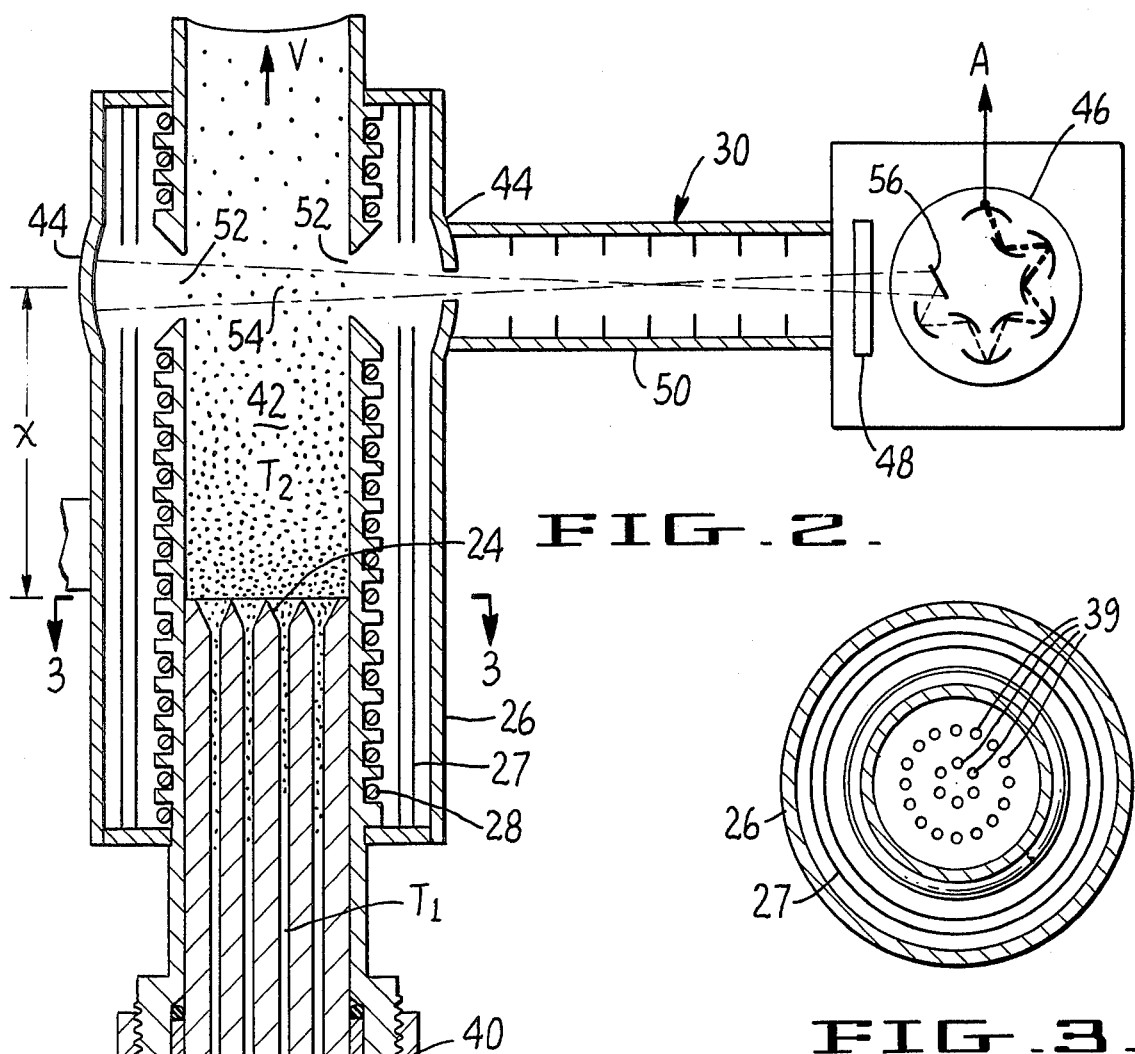
FIG. 2 is a cross-sectional pictorial view of a gas handling and detector assembly employed in an embodiment of the present invention.

FIG. 2 is a cross-sectional pictorial view of gas handling and detector assembly in which structure similar to those of FIG. 1 are indicated by like numerals. The gas handling and detector assembly, as depicted in FIG. 2, includes a portion of the conduit 18 for introducing gas-suspended particles into the burning chamber 26. The detector assembly, denoted generally by the numeral 30, is attached to the burning chamber 26.

As shown in the FIG. 2, the conduit 18 is formed with plural passages 39 through which the gas-suspended particles pass. Advantageously, the flow of the particles into the burning chamber is laminar as discussed above. Within the conduit, the gas-suspended particles are maintained at a temperature $T_1$, selected so that the particles of interest do not burn prior to entry into the burning chamber. The passages terminate in inlets 24 for the burning chamber. The inlets constitute widened portions of the passages in the conduit 18 which accommodate the expansion of gas due to the heat provided in the burning chamber.

The conduit 18 is slideably mounted within the burning chamber by a sliding seal 40 to permit relative movement of the conduit with respect to the burning chamber and limit leakage of the gas-suspended particles.

The inner wall of the burning chamber is placed in thermal contact with a suitable heating means 28, for example an electrical resistance heating element such as a flexible, elongated electrical resistance wire encapsulated in a coaxial sheath. As indicated in FIG. 2 the heating element heated zone 42 in the burning chamber to temperature $T_2$. Temperature $T_2$ is a temperature sufficient to cause incandescent burning of the gas-suspended particles and is, advantageously, selected to be high enough so that the burning of the gas-suspended particles does not significantly increase the temperature within the burning zone 42.

Figure 3:
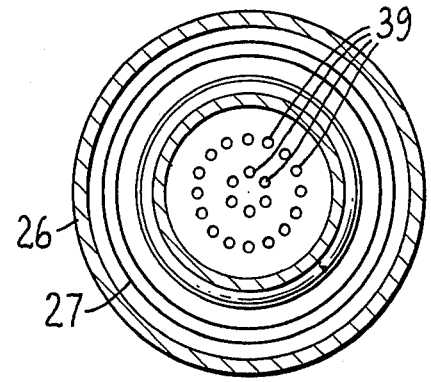
FIG. 3 is a cross-sectional view of the gas handling arrangement of FIG. 2 taken in the direction of arrows 3—3.

The detector assembly 30 may include a cooled mirror 44 attached to exterior housing 26, which is shielded by heat shield 27 from the temperature and burning chamber 26 by concentric metal foil shields extending around the periphery of burning chamber 26. This arrangement is also shown in FIG. 3, which is a cross-sectional view of the apparatus of FIG. 2, taken in the direction of arrows 3—3 and in which like structures are identified with like numerals. The detector assembly 30 also includes photomultiplier tube 46.

In front of photomultiplier tube 46 lies a light filter 48 and a baffled tube 50 for collimating radiant energy from the heated zone 42. Radiant energy from the heated zone 42 passes to the cooled mirror 44 via a circumferential aperature 52 in the heated chamber. The optical parameters of the detector define a detection zone 54 within the heated zone 42. Radiant energy from the incandescent burning of particles within the detected zone 54 radiates to the circumferential mirror 44 and tube 50 through the aperature 52. The light is collimated and filtered by filter 48 for selecting radiation yielding an optimum signal to noise ratio. The light finally impinges on the photocathode 56 of the photomultiplier tube. The arrangement of the mirror 44, aperatures 52 and baffle tube 50 is configured to optically shield the photocathode of the photomultiplier tube from exposure to surfaces of the heated chamber to exclude emissions from such surfaces and limit the radiant energy detected to the radiant energy emitted by the burning particles within the detection zone 54.

Radiant energy impinging on the photocathode 56 is amplified through a cascading action of electrons along the consecutive dynodes of the photomultiplier tube. An output signal related in value to the intensity of the radiant energy in the detected zone 54 appears at the output terminal a of the photomultiplier tube.

Figure 4:
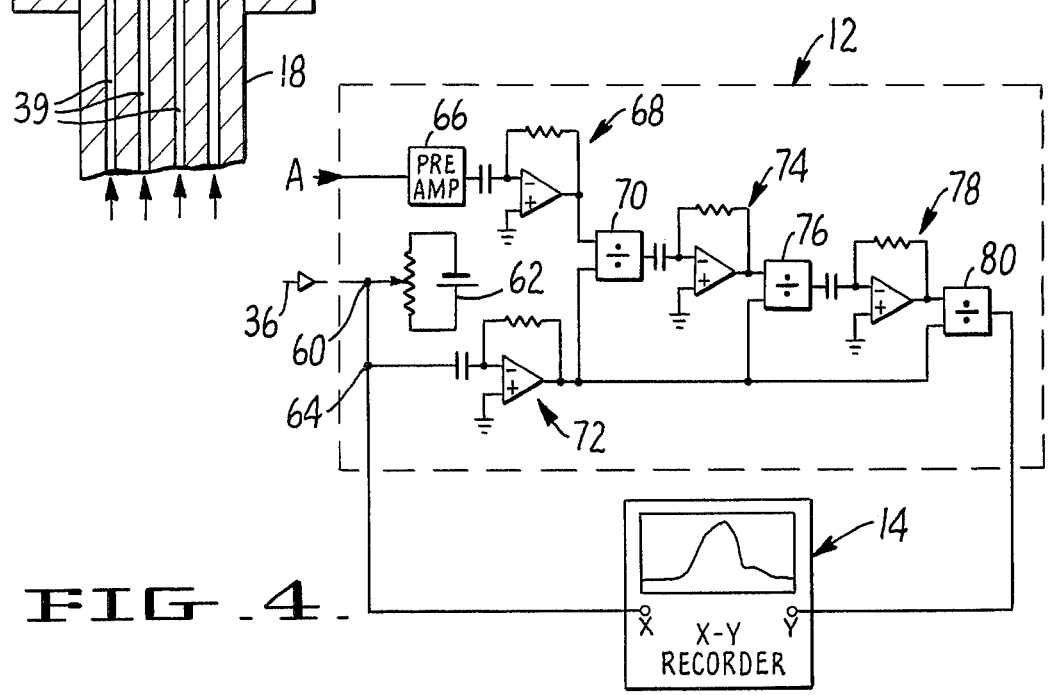
FIG. 4 is a schematic diagram of a processing circuit and recorder arrangement employed in an embodiment of the present invention.

Referring now to FIG. 4, an embodiment of the processing circuits 12 and recorder 14 is described in detail. For the sake of clarity, the present invention is described in terms of an analog electrical system of amplifiers and divider circuits. It will be obvious that in actual practice microprocessors or other digital computer means may be used to perform each of the arithmetic functions required to determine the results of the size distribution measurements.

The processing circuit 12 shown in FIG. 4 may receive an output electrical signal at terminal A from a photomultiplier tube such as that described in connection with FIG. 2. The processing circuit 12 may also receive an electrical or mechanical signal indicative of the distance x between the inlet 24 and detection zone 54. See FIG. 2. The particular circuit shown in FIG. 4 receives a mechanical signal functionally related to the relative positions of the inlet 24 and the detection zone 54 of FIG. 2. The mechanical signal, indicated schematically by dashed line 36 in FIG. 4, corresponds to a mechanical coupling of the relatively moving parts of the gas handling and photodetector assembly to a variable resistor 60. A supply voltage 62 is applied across the fixed terminals of the variable resistor 60 and a signal obtained at node 64 is proportional to the distance x between the inlet 24 and the detection zone 54.

The output signal of the photomultiplier tube, applied at terminal A of FIG. 4, is electrically amplified by a preamplifier 66. This signal is then differentiated by first differentiation circuit 68. An output signal of the first differentiation circuit 68 is applied to an input terminal of a first divider circuit 70. In a similar manner, the second differentiating circuit 72 differentiates the electrical signal occurring at node 64. An output signal of the second differentiating circuit 72 is applied as a divisor input signal to the first divider circuit 70. An output signal of the first divider circuit 70 is applied to a third differentiating circuit 74. An output signal of the third differentiating circuit 74 is applied to a second divider circuit 76. Likewise, the output signal of the second differentiating circuit 72 is applied as the divisor to the second dividing circuit 76. An output signal of the second divider circuit 76 is applied to a fourth differentiating circuit 78. The output signal of the fourth differentiating circuit 78 is applied to a third divider circuit 80. The output signal of the second differentiating circuit 72 is likewise applied as the divisor to the dividing circuit 80. Finally, an output signal of the third divider circuit 80 is applied to the chart recorder indicated generally by the numeral 14.

In a preferred embodiment, a signal from node 64 may be applied to control deflection along the x axis of the chart recorder 14, and the output signal of the divider circuit 80 may be applied to control the deflection along the y axis of the chart recorder 14. Application of the output signals from the processing circuit 12 in the manner shown in FIG. 3 may be used to provide a graphical representation of the size distribution of particles entrained in the gas introduced into the burning chamber. The deflection of the recorder along the y axis is proportional to the number of particles of a particular size and the deflection along the x axis is indicative of the radius of the particles measured.

Although the invention has been described with preferred embodiments, it is to be understood that variations and modifications may be resorted to as will be apparent to those skilled in the art. Such variations and modifications are to be considered within the purview and the scope of the claims appended hereto.

What is claimed is:
1. A method for measuring the size distribution of carbonaceous particles entrained in a gas comprising the steps of:
passing the entraining gas through a heated zone to induce incandescent burning of the particles, whereby the particles entrained in the gas are gradually consumed as the particles move through the heated zone;
detecting a portion of the electromagnetic energy emitted by the burning, entrained particles at varying locations along the path of flow of the gas through the heated zone; and
producing an indication of the size distribution of the particles entrained in the gas responsive to the rate at which the detected electromagnetic energy varies with detection location along the path of flow.

2. A method for measuring the size of incandescently burnable particles suspended in a gas comprising the steps of:
heating the particles to a temperature sufficient to cause incandescent burning of the particles;
detecting the intensity of radiant energy emitted by heated burning particles; and
providing an output signal, responsive to the detected intensity of radiant energy emitted by the burning particles, related in value to the third derivative of the intensity of emitted radiant energy with respect to time, said output signal providing an indication of the size of the detected burning particles.

* * * * *